United States Patent [19]

Hantmann

[11] Patent Number: 5,318,078

[45] Date of Patent: Jun. 7, 1994

[54] PROCESS FOR BOTTLING BEVERAGES

[75] Inventor: Bernhard Hantmann, Bergen, Fed. Rep. of Germany

[73] Assignee: Lang Apparatebau GmbH, Siegsdorf, Fed. Rep. of Germany

[21] Appl. No.: 678,368

[22] PCT Filed: Oct. 17, 1989

[86] PCT No.: PCT/EP89/01240

§ 371 Date: Jun. 25, 1991

§ 102(e) Date: Jun. 25, 1991

[87] PCT Pub. No.: WO87/05128

PCT Pub. Date: Aug. 27, 1987

[30] Foreign Application Priority Data

Oct. 26, 1988 [DE] Fed. Rep. of Germany ....... 3836465

[51] Int. Cl.[5] .................... G01N 27/02; G01N 27/06; G01N 33/14; G05D 21/02
[52] U.S. Cl. ............................ 141/1; 141/83; 141/89; 141/91; 141/192; 222/1; 222/52; 222/54; 222/148; 137/5; 324/439; 324/441; 324/445; 436/20; 436/24
[58] Field of Search ............... 141/1, 83, 89, 91, 192; 222/1, 52, 54, 148; 137/5; 324/439, 441, 445; 134/113; 436/20, 22-24

[56] References Cited

U.S. PATENT DOCUMENTS

| | | | |
|---|---|---|---|
| 3,820,014 | 6/1974 | Ludt | 137/5 X |
| 4,626,833 | 12/1986 | Schlaich | 324/439 X |
| 4,733,798 | 3/1988 | Brady et al. | 222/23 |
| 4,976,137 | 12/1990 | Decker et al. | 324/439 |
| 5,156,298 | 10/1992 | LaRue | 222/52 X |

FOREIGN PATENT DOCUMENTS

| | | | |
|---|---|---|---|
| 2001563 | 4/1990 | Canada | 324/439 |
| 1158727 | 12/1963 | Fed. Rep. of Germany . | |
| 3400129 | 3/1985 | Fed. Rep. of Germany . | |
| 4134549 | 4/1993 | Fed. Rep. of Germany | 436/23 |
| 8705128 | 8/1987 | PCT Int'l Appl. | 222/52 |

OTHER PUBLICATIONS

Advances in instrumentation, vol. 41, part 1, 1986, ISA, (Research Triangle Park, N.C., US) K. M. Queeney et al.: "Applications of a Microprocessor-based Electrodeless Conductivity Monitor", pp. 339-352.

Primary Examiner—J. Casimer Jacyna
Attorney, Agent, or Firm—Ernest G. Szoke; Wayne C. Jaeschke; Norvell E. Wisdom, Jr.

[57] ABSTRACT

The invention concerns a process for controlling and/or distinguishing liquids used in the brewing industry. To distinguish water, rinse water, different kinds of beer, and various non-alcoholic drinks with the help of technical measuring devices, a measuring instrument for monitoring or distinguishing the conductivity of the liquid concerned by inductive measurement is used.

9 Claims, 5 Drawing Sheets

PROCESS FOR BOTTLING BEVERAGES

BACKGROUND OF THE INVENTION

Field of the Invention

This invention relates to a process for bottling beers and other beverages from several tanks through a common pipe into which fresh water can be fed, this common pipe leading through valves to the filling station, to the residual beverage tank or to the wastewater pipe.

Statement Of Related Art

In view of the increasing demands being imposed by both national and European legislation, breweries are being increasingly forced to monitor and document the quality of bottled products to an even greater extent. The most important requirement in this regard is to be able to differentiate water, rinse water, various types of beer, and various alcohol-free beverages using industrial measuring instruments. In view of the exacting demands on the final result, reliable measurement has hitherto only been possible to a limited extent in terms of equipment and for reasons of hygiene, because the measuring instrument has to be fully cleanable and sterilizable and also maintenance-free and reliable. In addition, it has to lend itself to streamlined installation in production pipes while the measurement itself has to be geared to the monitoring of beer. Finally, monitoring has to be safely carried out "on-line" in the production process.

DESCRIPTION OF THE INVENTION

Summary of the Invention

According to the invention, these problems are solved in the process mentioned at the beginning in that the conductance of the liquid is measured inductively and, at the same time, its temperature is measured in the common pipe; in that, when the liquid flowing through the common pipe is changed, it is followed only by a liquid which, compared with the original liquid, has a greater conductance difference than the inductively measurable conductance variations of each of the two liquids and in that the valves are opened and closed in dependence upon the measured conductance.

For some years now, conductance measurement has had a firm place in bottle washing machines and in installations for monitoring the concentration of detergent solutions and for media separation of water and detergent solution. However, conductance measurement has never really been introduced as a variable in beer production processes. This is due above all to the fact that, hitherto, conductance measurements have only ever been carried out directly, i.e. galvanically, in beer production processes. The fact that conductance measurement is carried out inductively provides for far greater hygiene and cleanability.

Using this measuring instrument, it is possible to ensure that no water-diluted beers or beers containing residues of detergent solutions are included in the bottling process without too much undiluted and uncontaminated beer being discharged into the wastewater channel.

Since the conductance values of the liquids in question are largely temperature-dependent, the temperature of the particular liquid is determined at the same time. By means of temperature coefficients of the liquids determined in advance, variations in conductance can be corrected manually or automatically on the basis of variations in temperature.

Although a process for determining the concentrations of liquids by inductive conductivity measurement is known from DE-AS 11 58 727, the liquids in question therein are such liquids as, for example, concentrated hydrochloric acid where accuracy and hygiene requirements are not as stringent as in the case of foods. However, the present invention is concerned with beverages. When these beverages are bottled through a common bottling pipe, it is absolutely essential to ensure that a mixture of two beverages or residues of rinsing liquids are not bottled. It is also important to ensure that, after the common pipe has been rinsed with fresh water, no residues of the fresh water are included in the bottling, because this would reduce the concentration of the beverages.

In the prior art, accuracy problems arise, even in the measurement of concentrated acids, when the concentration is measured by conductivity inductively. On account of the considerably more stringent requirements in the case of foods, the inductive conductivity measuring process was, on the filing date of this application, to be judged far more critical by one skilled in the art in the case of the process for bottling beers and other beverages. In fact, this process had not even previously been used in breweries and bottling plants. Although, as mentioned above, trials with conductance measurements had been carried out in breweries, they were only ever carried out galvanically and, accordingly, led to hygiene problems so that conductance measurements were not pursued.

By contrast, it has been possible through the process according to the invention on the one hand to meet hygiene requirements and, on the other hand, to achieve the increased accuracy required in the processing of foods, as stipulated by legal limits, and still—by more exact change-over of the valves—to make savings through a smaller loss of beverages when the liquids are changed and a reduction in the wastewater containing the beverages.

DESCRIPTION OF PREFERRED EMBODIMENTS

Sudden but relatively small jumps in temperature can affect the measured values unless the temperature sensor, for example a platinum temperature sensor, projects directly into, or is thoroughly contacted by, the measuring medium. Accordingly, it is suggested that the temperature of the liquid flowing through the common pipe be measured by means of a temperature sensor having a short response time and a small mass.

In addition, it is of advantage to use a temperature sensor projecting freely into the liquid in the immediate vicinity of the conductance probe for temperature measurement.

In the event of prolonged interruptions in the flow of liquid, for example through closure of the valve during bottling, a slight evolution of small carbon dioxide bubbles can occur in the measuring channel of the conductance probe and reduce the conductance. To ensure that the conductance is not measured by the connected control unit when the valve is closed, it is suggested that a valve be provided to interrupt the flow of liquid and that the conductance only be measured when the liquid is flowing through the common pipe.

It has been found that the range of variation of the conductances of various beers and various types of alcohol-free beverages partly overlap and partly contrast distinctly with one another. Because of this, exact differentiation of all the various types, i.e. one type from another, is not possible. Nevertheless, the types which do not overlap in their range of variation can be significantly differentiated. Thus, beer/beer separation can readily be achieved when beers showing a marked conductance variation follow one another through a specific bottling sequence.

Figure 1:
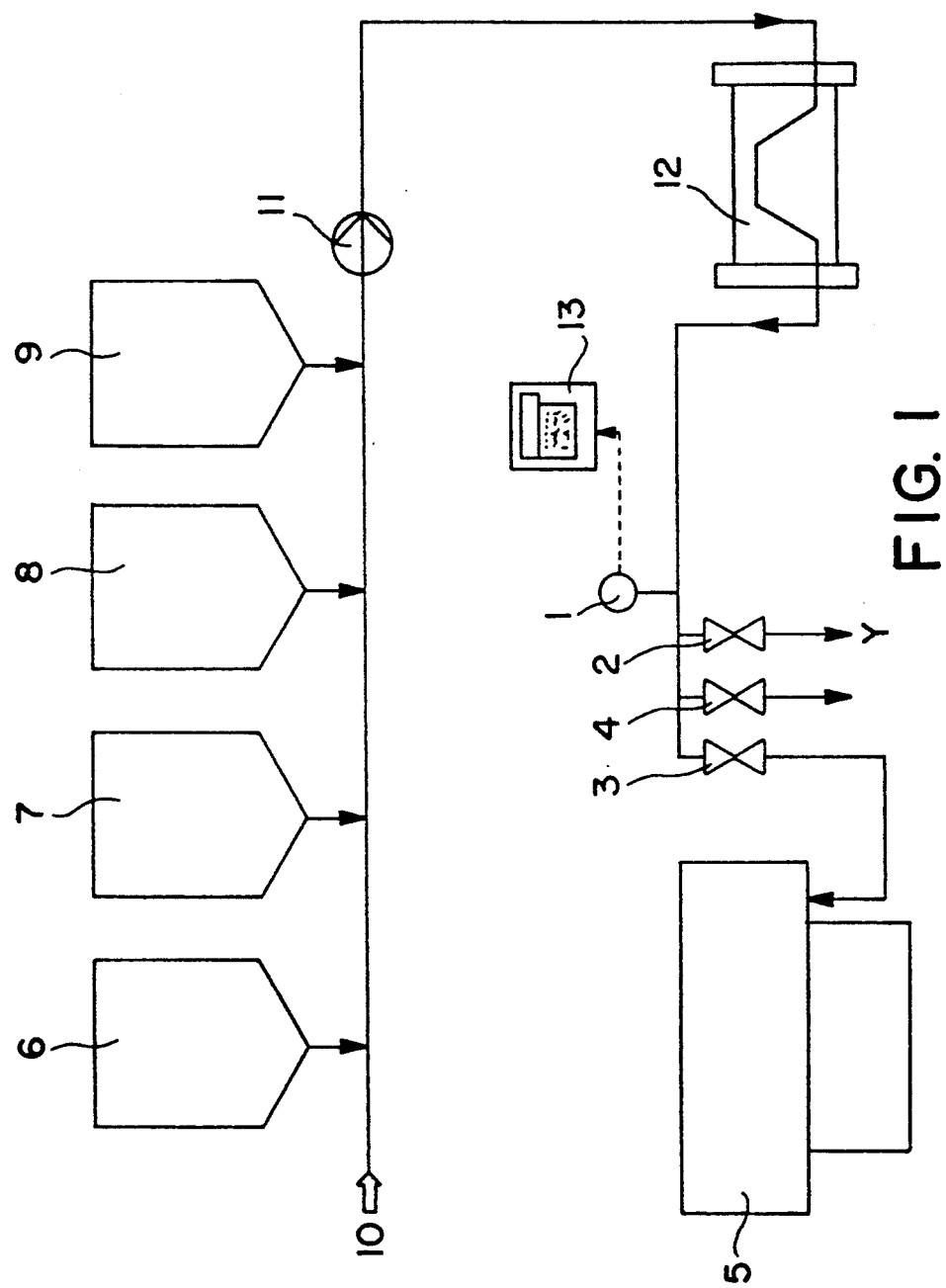
FIG. 1 is a schematic flow chart of a bottling plant in which the process according to the invention is applied.

There are various possibilities for using the measured conductances to control the production process. The most favorable variant in terms of cost is to install a conductance measuring instrument with display directly at the point of measurement in the bottling machine, the valve being changed over on the basis of the conductance reading and visual monitoring. Accordingly, it is generally suggested for the process according to the invention, where the valves regulating the liquid streams are manually operable, that a measuring instrument having an optical display of the conductance value be used for measuring conductance. This provides both for water/beer separation and for beer/beer differentiation. One example of an embodiment of this suggestion is shown in FIG. 1.

On the other hand, however, phase separation may also be automated. To this end, limit sensors are used to change over the valves. Accordingly, in the process according to the invention, which is applied to the bottling of beers and other beverages, where the valves which regulate the liquid streams and which guide the liquids into the waste water channel or into the bottle or barrel filler are designed to be controllable, it is suggested that the valves provided to divert the liquid into the filler, the residual beer tank, or the wastewater pipe be changed over from the wastewater channel to the filler and vice versa when a first conductance is reached and that the valves be changed over from the wastewater channel to the residual beverage tank and vice versa when a second conductance is reached. This proposal is particularly important for the bottling of alcohol-free beverages of which the conductance, in relative terms, is only just above that of the process water by comparison with beers. In this case, the switching level is situated between the conductance of the process water and the lowest conductances of the alcohol-free beverages.

Changing over when the second conductance is reached reduces loss through diversion of the liquid into the residual beer tank.

When the conductance rises to the second switching level, a signal is released to change over from the channel to the residual beer tank; when the conductance rises to the first switching level, the valves are changed over to the filling machine. The position is reversed in the event of decreasing conductance. The first switching level is below the range of variation of the individual beverages and higher than the second switching level.

To increase accuracy with the various types of beverage, it is suggested for the process according to the invention that, where the liquids have similar conductances, the valves be changed over when the same first and/or second conductance is reached. Accordingly, liquids having similar conductance values are combined into groups, the same first and/or second switching level being provided for each group. The group to which the beverage type to be bottled belongs may thus be manually preselected at a control console in order to adjust certain switching levels for changing over the valves.

In another embodiment of the invention, central monitoring for several filling machines is possible and advantageous. It is suggested in this regard that the measured-value signal be evaluated through a freely programmable control system with analog value processing. The switching level may be economically further differentiated by corresponding programming. In addition, inflow volume measurement with allocation (channel/residual beer tank/filler) and recording in conjunction with a through-flow counter are available for this purpose.

The measuring process according to the invention is made particularly accurate if the valves are controlled through the differences of the measured values of several measuring points. This more elaborate measurement and evaluation system is based on a comparison of the measured values of, for example, two measuring points, for example in a bottling system, the switching of the valves being controlled as a function of the percentage variations in the measured values and not by absolute values. The two measuring points in question are marked a and b in FIG. 5.

Accordingly, it is suggested that the conductance be measured simultaneously at several measuring points of the common pipe and that the valves be changed over in dependence upon the differences in conductance at the measuring points. This process provides for much greater accuracy during change-over because, through the differential measurement, the ranges of variation within a given type of beer are not relevant.

In this way, beer types can also be separated very exactly from one another without intermediate rinsing. More accurate determination of water dilutions and safe detection of the presence of even minimal quantities of detergent and disinfectant are also achieved.

One example of embodiment of the invention is described in detail in the following with reference to the accompanying drawings.

Several pressure tanks (6,7,8,9) opening into a common pipe are shown in FIG. 1. Fresh water (10) may also be fed into this pipe. The liquid in the pipe is pumped by a pump (11) through a short-time heater (12) and through a valve (3) to the bottle filler (5). Instead of to the bottle filler (5), the liquid may also be transported through a valve (2) or a valve (4) into the wastewater channel or into a residual beer tank.

Shortly before the liquid reaches the valves (2), (4) and (3), it passes the measuring point of the measuring instrument (1) which is connected to a recorder (13). On the chart recorder (13), the conductance and the temperature are recorded and evaluated as analog signals between 0 and 20 milliamperes.

According to the invention, the following differences may be reproducibly measured:

The difference between water, beer and alcohol-free beverages; the difference between a beer type a and a beer type b; dilution of the beer by water and contamination of the beer by detergent solutions.

So far as breweries are concerned, the first two points are of economic important for reducing rinsing losses during replacement processes and for reducing chemical oxygen demand by beverage residues. The last two aspects are important above all in regard to the strict obligation on the producer to ensure that the beverages are not contaminated by detergent solutions or diluted by water.

In the practical application of the invention, the temperature coefficients between the bottling temperature and the reference temperature for all beers and alcohol-free beverages were determined in the laboratory by means of a suitable measuring instrument. Depending on type, the measured TC values of these beverages vary by about 0.07% per °C. around a mean value of 2.32%/°C., which was set digitally for the conductance measurements.

Figure 2:
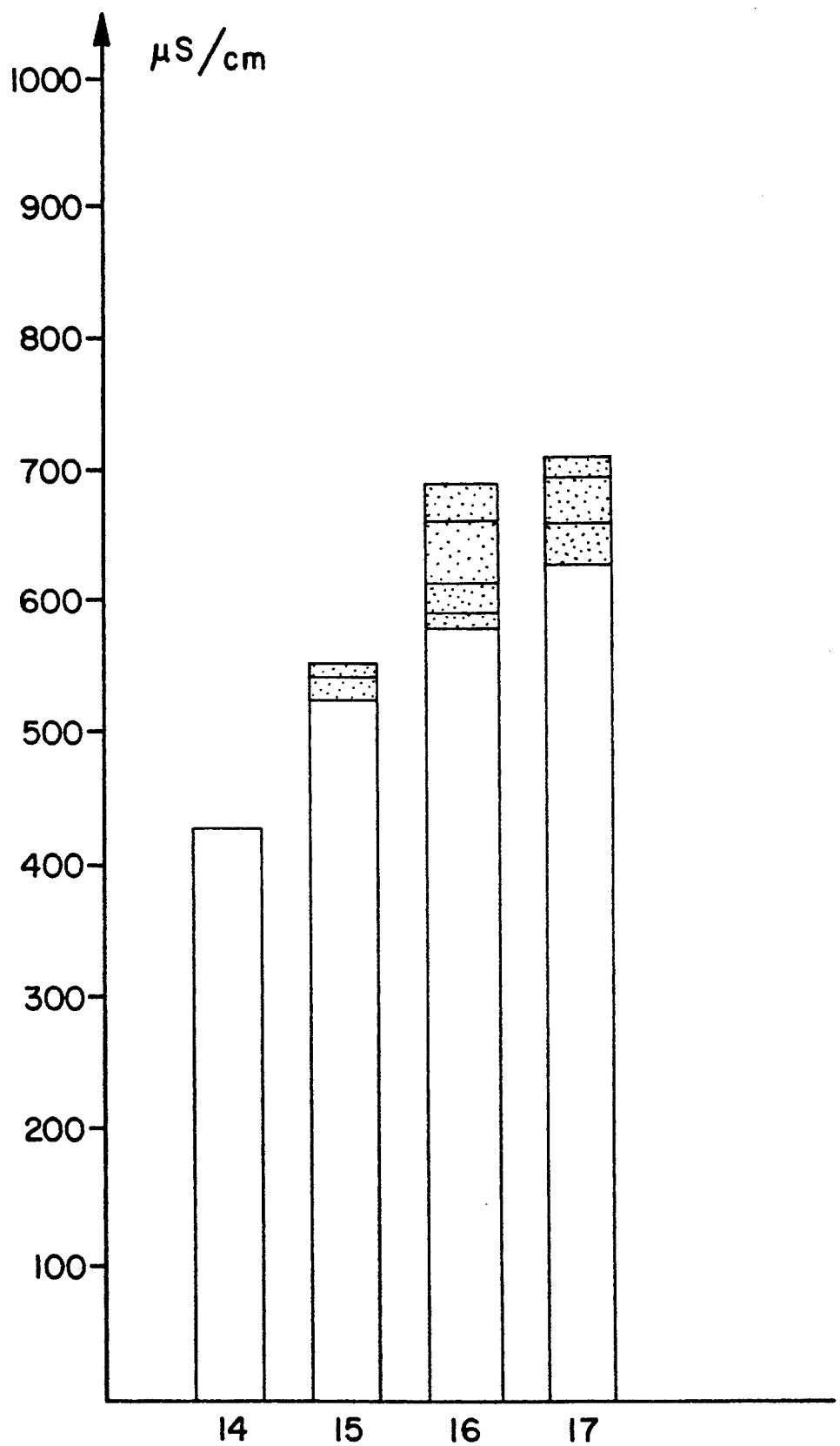
FIG. 2 is a graph of the conductances of process water and alcohol-free beverages.

The conductances of process water (14), lemonade (15), orangeade (16) and "Spezi" (17) are shown in the bar graph of FIG. 2. The conductances of these beverages are markedly above that of the process water so that phase separation between product and rinsing water is readily possible in this case. The conductances are shown in FIG. 2 in units of microsiemens per centimeter.

Figure 3:
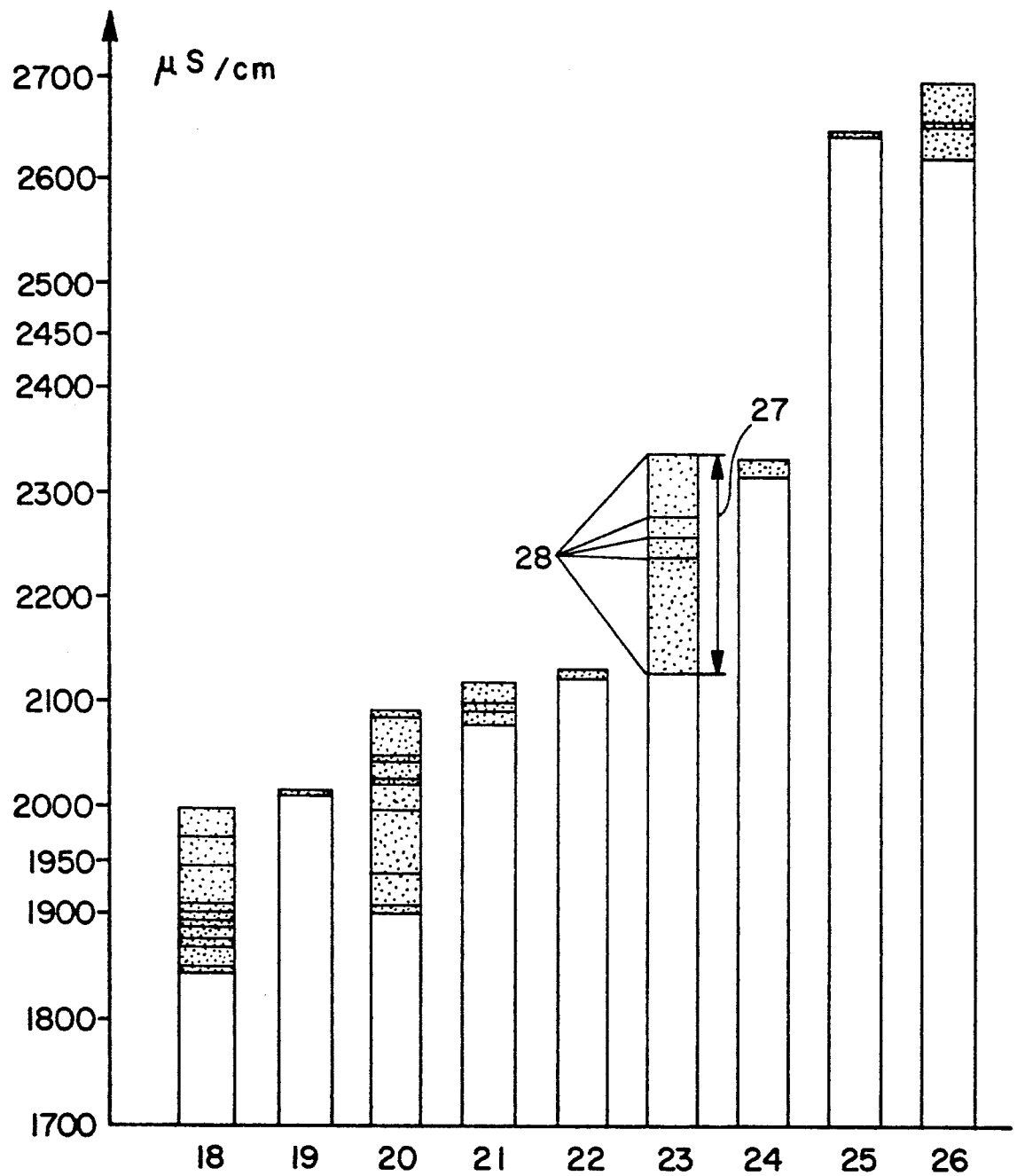
FIG. 3 is a bar graph showing the conductances of several beer types.

The conductances of the measured beer types "Hefeweißbier" (18), "Hell Lager" (19), "Pils" (20), "Hell Export" (21), "Dunkel" (22), "Märzen" (23), "Heller Bock" (24), "Doppelbock" (25) and non-alcoholic "Weißbier" (26) are shown in the bar graph in FIG. 3. The shaded area represents the range of variation of each type on different bottling days, a horizontal bar representing an individual result. However, the values per bottling batch are substantially constant. The range of variation is denoted by (27) and the individual measured values for the "Märzen" beer (23) by (28).

Depending on type, the beers with conductances between 1800 and 2700 microsiemens/centimeter are markedly above the process water with its conductance of 430 microsiemens/centimeter. In view of this difference, any type can be reliably distinguished from water and the water/beer mixed phase. However, the absolute values of the beers of a given type vary considerably on different bottling days and from different pressure tanks, in some cases by as much as 10%. The reason for this would appear to lie in the parameters of the brewing process, above all in the brewhouse.

Figure 4:
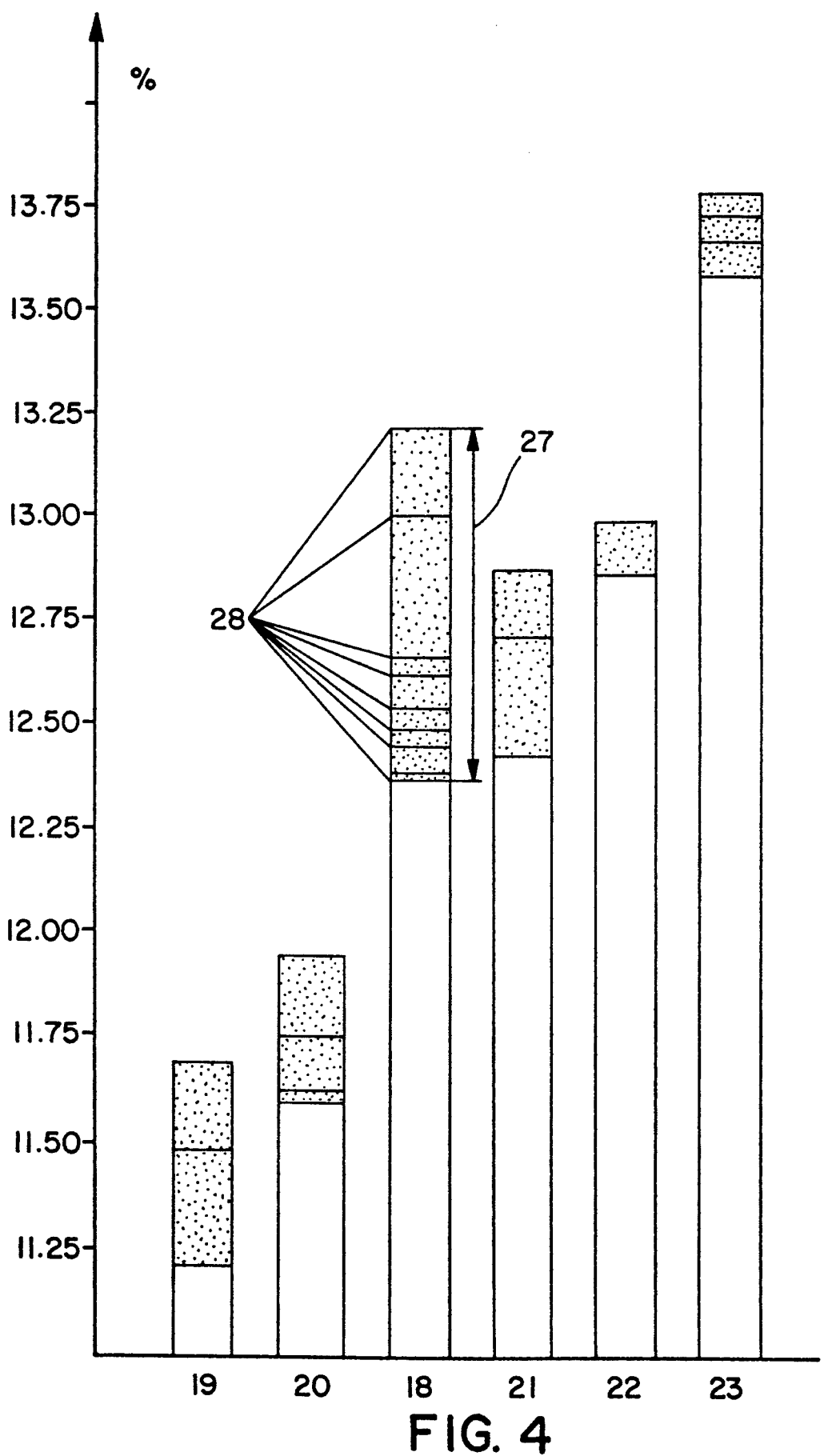
FIG. 4 shows the original wort contents of several beer types.

The original wort content of some beers is shown in FIG. 4. The reference numerals used correspond to those in FIG. 3. As can be seen, the comparative analyses of the original wort contents with the conductances of the beers show no connection between original wort content and conductance. Accordingly, conductance measurement cannot be reduced to measurement of the original wort content.

As suggested above, it is of advantage to divide the various beverages to be bottled into groups having similar conductances. In the case of the conductances shown in FIGS. 2 and 3, for example, the grouping may look as follows:

TABLE 1

| Group 1 | All alcohol-free beverages | Switching level 1 at | 500 µS/cm |
|---|---|---|---|
| Group 2 | Hefeweißbier Hell Lager | Switching level 2 at | 600 µS/cm |
| | Pils | Switching level 1 at | 1800 µS/cm |
| Group 3 | Hell Export Dunkel Märzen | Switching level 2 at | 600 µS/cm |
| | Heller Bock | Switching level 1 at | 2000 µS/cm |
| Group 4 | Doppelbock | Switching level 2 at | 600 µS/cm |
| | Weißbier, alcohol-free | Switching level 1 at | 2500 µS/cm |

By comparison with other measuring processes which are based directly or indirectly on the original wort content or on the degree of clouding, inductive conductance measurement offers an at least equally accurate, but far less expensive alternative. On account of the brewing process, the original wort contents vary and overlap, even within the various beer types, as shown in FIG. 4.

By virtue of the possibilities of variable measured value evaluation by freely programmable control systems, the conductance measuring system can be extended as required. In addition, it may be designed to release warning signals in the event of contamination by detergent or disinfectant.

As at the "bottle filler" stage described above, measurement and separation according to the same production aspects are both appropriate and economical in the following stages of the production process:

wort cooling (separation of water, worts, water)
filtration (separation of water, beer, beer, water)
bottle filler (separation of water, beer, beer, water, alcohol-free beverages, water) and
barrel/keg filling (separation of water, beer, beer, water).

Figure 5:
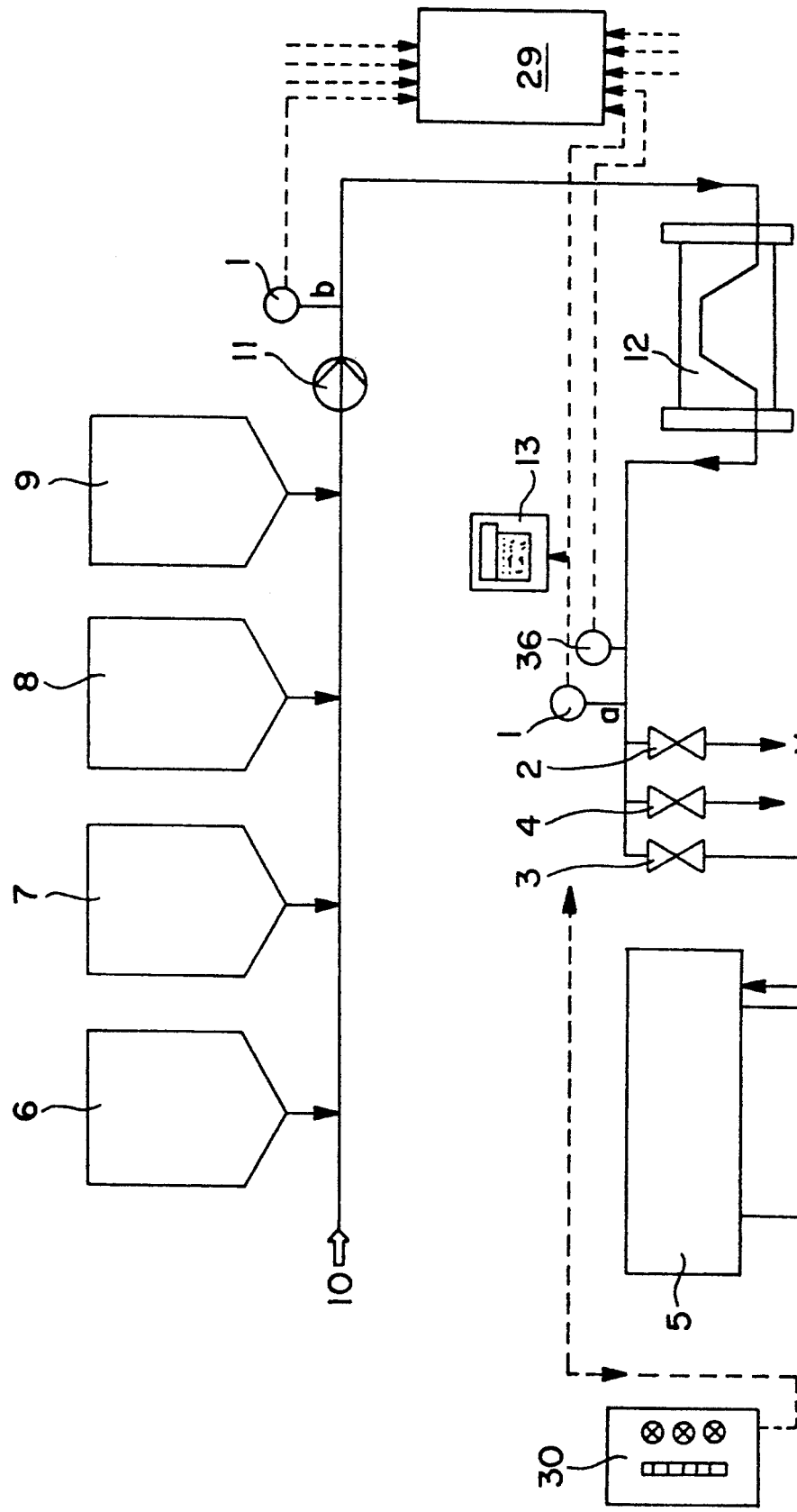
FIG. 5 is a schematic flow chart of a bottling plant in which the valves are controlled through the differences in the conductances of several measuring points.

FIG. 5 illustrates monitoring of the bottling process by differential value processing. The reference numerals have the same meanings as in FIG. 1. A central control console (29), to which the conductance measuring instruments (1) and the temperature sensor (36) are connected, and a control housing (30) with a connection to the central control console (29) are additionally shown in FIG. 5. The conductance is measured at several different points a, b of the pipe and the difference between the measured values is established. The measured value recorded at the valve is corrected by the temperature factor before-hand. To this end, the temperature of the liquid is measured by the thermocouple (36) in the vicinity of the measuring point a.

Through the installation of the conductivity measuring instrument at the entrance of the bottling plant, beer and alcohol-free beverages can be distinguished from water by the measurement of conductivity. The fulfillment of the following criteria in accordance with the invention is important to the application of the process in brewing:

The conductivity measuring system meets the requirement of monitoring beer, is maintenance-free and reliable, can be completely cleaned and sterilized, and can be incorporated into product conveying systems. Beer types can be differentiated when the production cycle of the brewery allows beer to be replaced by beer having different conductance levels.

I claim:

1. A process for bottling beverages from a plurality of tanks through a common pipe into which fresh water can be fed, said common pipe leading through a plurality of valves to a filling station, to a residual beverage tank and to a wastewater pipe, wherein: the conductance of the liquid is inductively measured at at least one point within the common pipe and, at the same time, the temperature of the liquid is measured in the common pipe; when the liquid flowing through the common pipe is changed, it is changed to a liquid which differs in conductance from the original liquid by an amount greater than the inductively measurable conductance variations of each of the two liquids; and at least one of said plurality of valves is opened when the measured value of the conductance at one point or the measured value of the difference in conductance between two different points reaches a preselected first conductance and is closed when the measured value of the conductance at one point or the measured value of the difference in conductance between two different points reaches a preselected second conductance.

2. A process as claimed in claim 1, wherein the temperature of the liquid flowing through the common pipe is measured by means of a temperature sensor having a short response time and low mass.

3. A process as claimed in claim 1, wherein a temperature sensor projecting freely into the liquid in the immediate vicinity of the conductance sensor is used for temperature measurement.

4. A process as claimed in claim 1, wherein the conductance is only measured when the liquid is flowing through the common pipe.

5. A process as claimed in claim 1, wherein the valves regulating the liquid streams are designed for manual actuation and a measuring instrument incorporating an optical display of the conductance is used for measurement.

6. A process as claimed in claim 1, wherein the valves provided to divert the liquid into the filler, the residual beer tank, and the wastewater pipe are changed over from the wastewater channel to the filler and vice versa when a first conductance is reached and in that the valves are changed over from the wastewater channel to the residual beverage tank and vice versa when a second conductance is reached.

7. A process as claimed in claim 6, wherein, where the liquids have similar conductances, the valves are changed over when the same first and/or second conductance is reached.

8. A process as claimed in claim 1, wherein the measured-value signal is evaluated via a freely programmable control system with analog value processing.

9. A process as claimed in claim 1, wherein the conductance is measured simultaneously at a plurality of measuring points of the common pipe and in that the valves are controlled on the basis of the differences between the measured values at different measuring points.

* * * * *